United States Patent [19]

Garfield et al.

[11] Patent Number: 5,698,738
[45] Date of Patent: Dec. 16, 1997

[54] N-NITROSO-N-SUBSTITUTED HYDROXYLAMINES AS NITRIC OXIDE DONORS

[75] Inventors: Robert E. Garfield, Friendswood; Alexandru T. Balaban, Galveston; William A. Seitz, Dickinson; Douglas J. Klein, Galveston; Melanie Lesko, Friendswood, all of Tex.

[73] Assignees: Board of Regents, The University of Texas System; The Texas A&M University System

[21] Appl. No.: 440,970

[22] Filed: May 15, 1995

[51] Int. Cl.⁶ .................. A61K 31/135; C07C 243/06
[52] U.S. Cl. .................. 564/112; 514/567; 514/611; 562/434
[58] Field of Search ................... 514/567, 611; 562/434; 564/112

[56] References Cited

U.S. PATENT DOCUMENTS

| | | | |
|---|---|---|---|
| 3,813,249 | 5/1974 | Ezekiel et al. | 96/67 |
| 4,535,154 | 8/1985 | Keefer et al. | 544/106 |
| 4,954,526 | 9/1990 | Keefer | 514/611 |
| 5,039,705 | 8/1991 | Keefer et al. | 514/611 |
| 5,155,137 | 10/1992 | Keefer et al. | 514/611 |
| 5,185,376 | 2/1993 | Diodati et al. | 514/611 |
| 5,208,233 | 5/1993 | Keefer et al. | 514/231.8 |
| 5,212,204 | 5/1993 | Keefer et al. | 514/647 |
| 5,250,550 | 10/1993 | Keefer et al. | 514/357 |

FOREIGN PATENT DOCUMENTS

2 054 661  5/1972  Denmark.

OTHER PUBLICATIONS

Ahokas et al., "Enhanced Endothelium–Derived Relaxing Factor Activity in Pregnant Spontaneously Hypersensitive Rats," *Am. J. Obstet. Gynecol. (Abstract),* 164(1):242, Jan., 1991.

Balaban et al., "N–Nitroso–Phenyl–Nitroxide," *Revue Roumaine de Chimie,* 16(5):721–723, 1971.

Balaban, "Stable Nitrogen Free Radicals," *Revue Roumaine de Chimie,* 16(5):725–737, 1971.

Balaban and Negoțiā, "Factors Affecting Stability and Equilibria of Free Radicals. VII Arenesulphonyl–Phenyl–Nitroxides and 1–Anenesulphonyl–2,2–Diphenylhydrazyls," *Revue Roumaine de Chimie,* 17(7):1227–1234, 1972.

Balaban and Istrătoiu, "N–Arenesulphonyl–N–(2,2,6,6–Tetramethylpiperidyl–1)–Aminyls, Hydrazyls with No Nitrogen–Bonded Aromatic Groups," *Tetrahedron Letters,* 21:1879–1880, Apr., 1973.

Balaban et al., "Aryl–N–nitroso Nitroxides," *Journal of Magnetic Resonance,* 9;1–7, 1973.

Balaban et al., "Model MNDO Calculations For Rotamers of α–Acylnitroxides and of N–Nitrosonitroxides," *Tetrahedron,* 43(2):405–408, 1987.

Bredt and Snyder, "Isolation of nitric oxide synthetase, a calmodulin–requiring enzyme," *Proc. Natl. Acad. Sci. USA,* 87:682–685, Jan., 1990.

Culotta and Koshland, Jr., "NO News is Good News," *Science,* 258:1862–1865, Dec., 1992.

Diodati et al., "Complexes of Nitric Oxide with Nucleophiles as Agents for the Controlled Biological Release of Nitric Oxide: Hemodynamic Effect in the Rabbit," *Journal of Cardiovascular Pharmacology,* 22:287–292, 1993.

Drago et al., "A Mechanism for the Reaction of Diethylamine with Nitric Oxide," *J Am Chem Soc,* 83:4337–4339, Nov., 1961.

Drago and Karstetter, "The Reaction of Nitrogen(II) Oxide with Various Primary and Secondary Amines," *J Am. Chem. Soc.,* 83:1819–1822, Apr. 1961.

Drago, "Reactions of Nitrogen(II) Oxide," *Amer. Chem. Soc.,* Ch. 15, pp. 143–149, 1962.

Feelisch, "Biotransformation to nitric oxide of organic nitrates in comparison to other nitrovasodilators," *European Heart Journal,* 14(Supp. I):123–132, 1993.

Feelisch, "The Biochemical Pathways of Nitric Oxide Formation from Nitrovasodilators: Appropriate Choice of Exogenous NO Donors and Aspects of Preparation and Handling of Aqueous NO Solutions," *Journal of Cardiovascular Pharmacology,* 17(Suppl. 3):S25–S33, 1991.

Furchgott and Zawadzki, "The obligatory role of endothelial cells in the relaxation of arterial smooth muscle by acetylcholine," *Nature.* 288;373–376, Nov., 1980.

Garfield and Yallampalli, "Control of Myometrial Contractility and Labor," *In: Basic Mechanisms Controlling Term and Preterm Birth,* K. Chwalisz, R.E. Garfield, (Eds.), Ernst Schering Research Foundation Workshop 7, Springer–Verlag, pp. 1–28, 1993.

Hansen et al., "N–Nitrosation of Secondary Amines by Nitric Oxide Via The 'Drago Complex'," National Cancer Institute, Bethesda, MD, pp. 21–29, 1980.

Ignarro, "Signal Transduction Mechanisms Involving Nitric Oxide," *Biochemical Pharmacology,* 41(4):485–490, 1991.

Iida et al., "Reactions of nitrosobenzenes with nitrogen monoxide," *Chemistry Abstracts,* The American Chemical Society, 89(21):573, Abstract No. 179627x, Nov., 1978.

Isono et al., "Effect of FK409, a Novel Nitric Oxide Donor, on Acute Experimental Myocardial Ischemia," *Japan. J. Pharmacol.,* 62:315–324, 1993.

(List continued on next page.)

Primary Examiner—Peter O'Sullivan
Attorney, Agent, or Firm—Arnold, White & Durkee

[57] ABSTRACT

Nitric oxide has proved to mediate many important physiological processes. The nitric oxide donors of the present invention have a NONOate anion linked to an ortho-substituted aryl, a heteroaromatic substituent, asteroid, or a catecholamine. Preferred ortho substituents are alkoxy, halo, and alkyl. The cation of the salt is an alkali metal, an alkaline-earth metal, an ammonium or substituted ammonium group. Nitric oxide donors provided herein are more stable than that of nitrogen-bonded NONOates described previously. The by product left after release of NO, and the nitric oxide donors themselves, are very probably less carcinogenic than the corresponding nitrogen-bonded NONOates.

2 Claims, 6 Drawing Sheets

OTHER PUBLICATIONS

Izumi et al., "Gestational changes in L-arginine-induced relaxation of pregnant rat and human myometrial smooth muscle," *Am. J. Obstet. Gynecol.*, 169(5):1327–1337, Nov., 1993.

Kamm and Marvel, "B-Phenylhydroxylamine (Hydroxylamine, N-hhenyl-) $C_6H_5NO_2+2Zn+2ZnO$," *Org. Synth. Coll.*, 8(1):445–447, 1941.

Kasten et al., "Potentiation of osteoclast bone–resorption activity by inhibition of nitric oxide synthase," *Proc. Natl. Acad. Sci. USA*, 91:3569–3573, Apr., 1994.

Keefer et al., "Chemistry of the NONOates", *In: Nitrosamines and Related N–Nitroso Compounds*, 204th National Meeting of the American Chemical Society, ACS Symposium Series, R. Loeppky, C. Michejda, Eds., Ch. 11, pp. 137–146, 1994.

Keefer, "N–oxy–N–nitrosamine derivatives, their preparation, and their use as antihypertensive," *Chemical Abstracts*, The American Chemical Society, 113(17):71, Abstract No. 1453446, Oct., 1990.

Knowles and Moncada, "Nitric oxide as a signal in blood vessels," *TIBS*, 17:399–402, Oct., 1992.

Koshland, Jr., "The Molecule of the Year," *Science*, 258:1861, Dec., 1992.

Lees et al., "Arrest of preterm labour and prolongation of gestation with glyceryl trinitrate, a nitric oxide donor," *The Lancet*, 343:1325–1326, May, 1994.

Longhi et al., "Reactions of Nitrogen(II) Oxide with Miscellaneous Lewis Bases," *Inorganic Chemistry*, 1(4):768–770, Nov., 1962.

Maragos et al., "Complexes of NO with Nucleophiles as Agents for the Controlled Biological Release of Nitric Oxide. Vasorelaxant Effects," *Abstract*, MED, Abstract No. 63, 1992.

Marvel and Kamm, "Cupferron," *Org. Synth. Coll.*, 8(1):177–179, 1941.

Minisci and Galli, "Comunicazioni brevi," *Chimica e Industria (Milano)*, 46:423, 1964.

Moncada et al., "Nitric Oxide: Physiology, Pathophysiology, and Pharmacology," *Pharmacological Reviews*, 43(2):109–142, 1991.

Negoita et al., "N–(2,4,6–Tricarbomethoxyphenyl)–Alkoxyaminyls, New Push–Pull Stable Nitrogen Free Radicals," *Tetrahedron Letters*, 21:1877–1878, 1973.

Pinto et al., "Endothelial–derived relaxing factor released by endothelial cells of human umbilical vessels and its impairment in pregnancy–induced hypertension," *Am. J. Obstet. Gynecol.*, 164(2):507–513, Feb., 1991.

Ragsdale et al., "Decomposition of the Adducts of Diethylamine and Isopropylamine with Nitrogen(II) Oxide," *Inorganic Chemistry*, 4(3):420–422, Mar., 1965.

Preeclampsia: "An endothelial cell disorder," *Am. J. Obstet. Gynecol.*, 161(5):1200–1204, Nov., 1989.

Robert et al., "Preclampsia: An endothelial cell disorder," *Am. J. Obstet. Gynecol.*, 161(5):1200–1204, Nov., 1989.

Saavedra et al., "Secondary Amine/Nitric Oxide Complex Ions, $R_2N[N(O)NO]^-$. O–Functionalization Chemistry," *J. Org. Chem.*, 57(23):6134–6138, 1992.

Sand and Singer, "Stickoxyd und das Grignard'sche Reagens," *In: Justus Liebig's Annalen der Chemie*, C.F. Winter'sche Verlagshandlung, Leipzig, pp. 190–195, 1903.

Shukovski and Tsafriri, "The Involvement of Nitric Oxide in the Ovulatory Process in the Rat," *Endocrinology*, 135(5):2287–2290, 1994.

Smith, "Cupferron and Neo–cupferron,"GF Smith Chem. Co., Columbus, OH, 1938.

Sortino et al., "Involvement of Nitric Oxide in the Regulation of Gonadotropin–Releasing Hormone Release from the GT1–1 Neuronal Cell Line," *Endocrinology*, 134(4):1782–1787, 1994.

Stamler et al., "Biochemistry of Nitric Oxide and Its Redox–Activated Forms," *Science*, 258:1898–1902, Dec., 1992.

Yallampalli et al., "Nitric Oxide Inhibits Uterine Contractility During Pregnancy But Not During Delivery," *Endocrinology*, 133(4): 1899–1902, 1993.

Yallampalli and Garfield, "Inhibition of nitric oxide synthesis in rats during pregnancy produces signs similar to those of preeclampsia," *Am. J. Obstet. Gynecol.*, 169(5):1316–1320, Nov., 1993.

Yallampalli et al., "An L–arginine–nitric oxide–cyclic guanosine monophosphate system exists in uterus and inhibits contractility during pregnancy," *Am. J. Obstet. Gynecol.*, 170(1):175–185, Jan., 1994.

International Search Report dated Aug. 29, 1996.

N-NITROSO-N-SUBSTITUTED HYDROXYLAMINES AS NITRIC OXIDE DONORS

The present invention relates generally to methods for treatment of a variety of medical conditions with previous or new nitric oxide donors such as, for example, N-nitroso-N-substituted hydroxylamine or salts thereof.

BACKGROUND OF THE INVENTION

The concept that NO regulates many biological functions dates back only 15 years. In 1980, Furchgott and Zawadski first showed the endothelium must be intact for acetylcholine to produce vascular relaxation. Subsequently, numerous studies have shown that neurohumoral or pharmacological agents mediate vasodilation via the endothelium. It is now recognized that the endothelium releases a potent, labile, nonprostanoid vasodilating agent in response to various stimuli that either cause vasodilation or modulate vasoconstriction. This factor, originally termed endothelium-derived relaxing factor (EDRF), has been shown to be nitric oxide (NO) or a compound with a nitric oxide moiety.

NO is synthesized by the oxidative deamination of a guanidino nitrogen of L-arginine by at least three different isoforms of a flavin-containing enzyme, nitric oxide synthase (NOS) (Moncada, Palmer and Higgs, 1991). Three distinct isoforms have been purified, cloned (Bredt et al., 1990; Stuehr et al., 1991) and expressed, and there is evidence for the presence of NOS in almost every tissue of the mammalian body, albeit at widely different levels.

NO is an ideal local transcellular messenger because of its small size, lipophilic nature, and short duration of action. Commonly used chemical nitro-vasodilators, such as nitroglycerin and nitroprusside, appear to act by releasing NO.

Biological effects of NO. Nitric oxide elevates levels of cGMP (1,3,5-cyclic guanosine monophosphate) within vascular smooth muscle to produce relaxation and reduce the tone on blood vessels (Moncada, et al., 1991). Nitric oxide binds to heme and thus activates soluble guanylate cyclase (ignarro, 1991) to increase cellular content of cGMP. It has long been recognized that nitrovasodilators, such as nitroprusside and nitroglycerin, inhibit vascular smooth muscle contractility to produce relaxation or reduce vascular tone. These agents have been used since the late 1800's as vasodilators. However, it has only been recently that the mechanism of action of these compounds has been realized. Nitrovasodilators are now classified as nitric oxide donors (Moncada, et al., 1991). The long-used nitrovasodilators may be regarded as substitution therapy for a failing physiological mechanism. Nitric oxide is also produced by macrophages and other immune cells (Stuehr, et al., 1991). Stimulated macrophages produce nitric oxide from L-arginine and it is considered the first line of defense against invading pathogens.

There is a substantial body of evidence from animal experiments that a deficiency in nitric oxide contributes to the pathogenesis of a number of diseases, including hypertension, atherosclerosis and diabetes (Moncada, Palmer and Higgs, 1991). There are many recent studies showing that inhibition of nitric oxide synthase dramatically increases blood pressure. Inhibition of nitric oxide synthesis with L-NMMA (L-N$^G$methyl arginine), L-NA (L-N$^G$nitroarginine), or L-NAME (L-N$^G$nitroarginine methyl ester) causes long-lasting elevation in blood pressure and suggests that a reduction in the synthesis of nitric oxide may contribute to the pathogenesis of hypertension (Moncada, et al., 1991).

Further, in patients with pregnancy-induced hypertension, release of nitric oxide by umbilical vessels in lessened (Pinto et al., 1991) and the physiological decrease in blood pressure in pregnant spontaneous hypertensive rats was shown to depend on endothelial nitric oxide (Ahokas, et al., 1991). Additionally, infusion of L-NA increases blood pressure in pregnant rats and potentiates responses to vasopressors (Molnar, et al., 1992). These studies suggest that impaired nitric oxide synthesis may be an important mechanism in the etiology of pregnancy-induced hypertension (preeclampsia). Indeed, inhibition of NO in pregnant rats produced symptoms identical to preeclampsia (Yallampalli, et al., 1993). It has been suggested that preeclampsia is an endothelial cell disorder (Roberts et al., 1989). Nitric oxide is also produced by the uterine wall and it effectively inhibits uterine contractility during pregnancy but not during delivery (Yallampalli, et al. 1993). On the other hand, steroid hormones seem to regulate the nitric oxide-cGMP relaxation mechanism in the uterus (Yallampalli, et al., 1993).

Nitric oxide is also involved in the control of blood clotting. Nitric oxide is a very potent inhibitor of coagulation and this action may be extremely important in preventing clotting in the placental circulation. Previously, it has been suggested that prostacyclin regulates placental clotting. However, nitric oxide may be very important in this process either in conjunction with the inhibitory effects of prostacyclin or acting alone. Nitric oxide has been found to be synthesized in almost all tissues of the body including brain and peripheral nervous systems, smooth muscle vascular tissue, (see above), kidney, lung, uterus, etc.

Nitric oxide modulates various biological phenomena including regulation of smooth muscle contractility of several tissues. In previous studies, rat uterine tissues in vitro were examined to determine whether a L-arginine-nitric oxide-cGMP system is present in the rat uterus (Garfield and Yallampalli, 1993; Yallampalli et al., 1993; Izumi, et al., 1993). These studies reported that (1) the substrate and a donor of nitric oxide produced uterine relaxation, (2) inhibitors of the nitric oxide—cGMP pathway blocked the relaxation responses, (3) nitric oxide synthase was localized to several uterine cell types, (4) nitric oxide was produced by the uterus during periods when L-arginine was consumed and citrulline levels increased, (5) effects of nitric oxide substrate on relaxation were mimicked by cGMP, (6) the responses to L-arginine and NO were decreased during term and preterm labor, and (7) the NO synthetase isoforms are present in the uterus and upregulated during pregnancy but decreased when labor begins. These studies indicate that NO may control uterine contractility during pregnancy.

Present NO Donors: Presently, there are only a few nitric oxide donor compounds that are used clinically (e.g., nitroglycerin, sodium nitroprusside and amyl nitrite). Table 1 indicates various NO donor agents with clinical potential.

In a recent patent, Keefer (1993) included, in addition to aminoNONOates that he had reviewed, and whose structure he had proved by X-ray crystallography (Saavedra et al., 1992), cupferron, some derivatives as potential hypotensive agents. In a more recent review, Keefer indicated that when the NONO group is attached to a carbon atom as in cupferron, the parent N-aryl-N-nitroso-hydroxylamine is stable under protonating conditions, implying that unlike aminoNONOates which release NO readily, cupferron and its derivatives would act more sluggishly or not at all (Keefer et al. 1994).

TABLE 1

Present NO Donor Compounds

| Generic name | Trade name or synonym | Route of administration | Dose | Onset of action | Duration |
|---|---|---|---|---|---|
| Amyl nitrite | | Inhalation | 0.3 ml | 30–60 sec | 3 min |
| Nitroglycerin | Glyceryl trinitrate | Sublingual | gr 1/150; 0.4 mg | | |
| | | Oral | 2.5–6.5 mg | 30–60 min | 8–12 hr |
| | | Transdermal | 0.1–0.4 mg/hr | 2 hrs | 12 hrs |
| Pentaerythritol tetranitrate | Peritrate | Sublingual | 10 mg | 10 min | 30 min |
| | Pentritol | Oral | 60 mg | 30 min | 12 hr |
| | Pentafin | Oral | 10–20 mg | 30–60 min | 4–5 hr |
| | Vasitol | Sustained-release | 80 mg | 30–60 min | 12 hr 2–4 hr 4 hr |
| Erythrityle tetranitrate | Cardilate | Sublingual | 5–30 mg | 5–10 min | 2–4 hr |
| | Tetranitrol | Oral | 5–30 mg | 30 min | 4 hr |
| | Erythrol tetranitrate | Oral | 5–30 mg | 30 min | 2–4 hr |
| Isosorbide dinitrate | Isordil | Sublingual, oral | 5–10 mg 5–30 mg | 2 min 15–30 min | 1.5–2 hr 4 hr |
| Trolnitrate phosphate | Metamine | Oral | 2–10 mg | Slow, 3 days | Up to 1 wk |
| Dipyrimadol | Persantin | Oral | 25–50 mg | 2–5 min | 20–30 min |
| Nitroprusside | Nipride | i.v. | 10 µg/kg | 10 sec. | 5 min |

Uses of Nitric Oxide Donors: Presently, nitric oxide donors (nitroglycerin or amyl nitrite) are used for angina pectoris due to coronary artery disease and control of blood pressure associated with myocardial infarction or surgical procedures (nitroglycerin or sodium nitroprusside).

Nitric oxide (NO) donors presently in use consist either of substances which are nitrite or nitrite esters (e.g. amyl nitrate and glycerol-trinitrate), or inorganic nitroso complexes (e.g. sodium nitroprusside). In addition to these clinically used compounds, the so-called NONO-compounds which were prepared initially by Drago et al. (1961) from gaseous NO and secondary amines have been studied. Among the latter compounds, substances such as the diethylamine-nitric oxide addition compound have the drawback that they may decompose, leading to compounds that are proved carcinogens (dialkyl-nitrosoamines), along with the desired nitric oxide.

Problems with present nitric oxide donor compounds include the following:
a. Short duration of action
b. Short half-life
c. Lack of tissue specificity
d. Development of tolerance
e. Accumulation of toxic substances—e.g. cyanide from sodium nitroprusside
f. Compounds with a chain of three nitrogen atoms (i.e. having the NONO group attached to a nitrogen atom), on releasing nitric oxide, leave a remaining nitrosoamine fragment which may be carcinogenic in some cases.

Because of all of the above problems, known procedures are not completely satisfactory, and persons skilled in the art have searched for improvements.

Desirable qualities of new nitric oxide donor compounds are:
a. Long duration of action
b. Ease of use-oral preparation
c. Tissue selectivity
d. Lack of tolerance
e. Low toxicity One object of the present invention is to provide a method of use of N-nitroso-N-substituted hydroxylamines or salts thereof as nitric oxide (NO) donors having at least some of these qualities.

SUMMARY OF THE INVENTION

The present invention describes the use of certain N-nitroso-N-substituted hydroxylamines and salts thereof (1) as new nitric oxide (NO) donors. Also part of the present invention are uses of these new NO donors in a variety of medical disorders including uterine muscular disorders, hypertension and cardiovascular problems. Even prior NO donors have been found to have a new use in treating uterine muscular disorders.

The present invention provides nitric oxide donor compounds having the following structure:

R is an ortho-substituted aryl, a heteroaromatic substituent, a steroid, or a catecholamine; and M is an alkali metal, an alkaline-earth metal, an ammonium or substituted ammonium cation, wherein the compound decomposes under physiological conditions to release nitric oxide.

The ortho-substituted aryl may be 2-methylphenyl, 2-methoxyphenyl, 2-ethylphenyl, 2-isopropylphenyl, 2,4-difluorophenyl, 2,5-difluorophenyl, 2-chlorophenyl, 2,3-dichlorophenyl, 2,4-dichlorophenyl, 2,5-dichlorophenyl, 2-bromophenyl, 5-fluoro-2-methylphenyl, 4-fluoro-2-methylphenyl, 4-choro-2-methylphenyl, or 3-chloro-2-methylphenyl. Preferably, the ortho-substituted aryl is 2-chlorophenyl or 2-methoxyphenyl.

The heteroaromatic substituent is thienyl, oxazolyl, thiazolyl, imidazolyl, pyrazolyl, a six-membered azaaromatic, 2,2,5,5-tetramethylpiperidine, 2,2,5,5-tetramethylpyrrolidine, proline, hydroxyproline, morpholine, or 3-azabicyclo[3.2.2]nonane or simple substituted derivatives of all such systems.

In preferred embodiments, the ortho-substituted aryl is α-naphthyl bearing a halo, alkyl or alkoxy substituent; or phenyl or α-naphthyl bearing a sulfonate or carboxylate group.

The substituents on the R group are chosen so as: (i) to modulate the NO releasing potency either by means of their electron releasing/accepting ability, or by means of their steric effects when situated in the proximity of the nitroso group; (ii) to modify the hydrophilic/lipophilic properties of the NO donors, or, (iii) to counteract their negative electric charge.

The cation M+ is preferably an alkali metal cation (most preferably sodium or potassium) although other physiologically and pharmacologically acceptable cations may be used. Such cations include calcium, magnesium, ammonium or ammonium substituted with lower alkyl (C1–C4), cycloalkyl (5- or 6-membered), benzyl or phenyl. The ammonium salts of compound 1 where R is phenyl or naphthyl are commercially available. Compound 1 where R=phenyl and $M^+$ is $NH_4+$ is known as cupferron, and compound 1 where R=α-naphthyl and $M^+$ is $NH_4^+$ is known as neocupferron; these are used as reagents in analytical chemistry, but their ammonium cations may make them toxic to mammals.

Preferred R groups are α-naphthyl, ortho-substituted phenyl or a heterocyclic aromatic ring. In a preferred embodiment, R is a biologically active moiety designed to target the NO releasing agent to a specific organ or tissue. Specific examples of biologically active moieties include steroids (such as progesterone and estrogen, e.g.) and epinephrine or other catecholamines and simple derivatives thereof.

A preferred embodiment is a compound having the structure where R is 2-methylphenyl, 2-methoxyphenyl, 2-ethylphenyl, 2-isopropylphenyl, 2,4-difluorophenyl, 2,5-difluorophenyl, 2-chlorophenyl, 2,3-dichlorophenyl, 2,4-dichlorophenyl, 2,5-dichlorophenyl, 2-bromophenyl, 5-fluoro-2-methylphenyl, 4-fluoro-2-methylphenyl, 4-choro-2-methylphenyl, or 3-chloro-2-methylphenyl; and M is an alkali metal, an alkaline-earth metal, an ammonium or substituted ammonium cation, wherein the compound decomposes under physiological conditions to release nitric oxide. A further preferred embodiment is where R is 2-chlorophenyl or 2-methoxyphenyl.

Synthetic procedures for preparing compounds (1) include the steps of; reducing the corresponding nitro- or nitroso-compounds under conditions favoring the formation of N-aryl-hydroxylamines, followed by treatment with an alkyl nitrite and gaseous ammonia to obtain the corresponding ammonium salt, followed by ion exchange for preparing the alkali metal salts. Alternative methods for preparing compounds (1) involve (i) the reaction of aryl Grignard reagents with nitric oxide followed by treatment with ammonia or a reagent leading to the formation of alkali metal salt.; (ii) the spin trapping of nitric oxide with a nitroso derivative, yielding an isolable N-aryl-N-nitrosonitroxide, which can then be reduced to (1); (iii) the Sandmeyer reaction of aryldiazonium salts with nitric oxide (NO) in the presence of copper (II) and iron (II) salts, whereby an aryl radical reacts with NO leading to a nitroso derivative, followed by reaction with a second molecule of NO as in the preceding reaction.

Nitric oxide (either an overabundance or deficiency) is involved in many pathological problems such as preterm labor, climacterium, pregnancy-induced diabetes, postpartum hemorrhage, coronary artery disease, cancer and behavioral and digestive problems.

An embodiment of the present invention is a method of inhibiting uterine contractions in a subject comprising administering a therapeutically effective amount of a nitric oxide donor to the subject. A preferred nitric oxide donor is as described hereinabove.

A method of supplying nitric oxide to a subject comprising administering to the subject a pharmacologically effective amount of a compound having the structure is a further embodiment of the present invention. R is an ortho-substituted aryl, a heteroaromatic substituent, asteroid, or a catecholamine; and M is an alkali metal, an alkaline-earth metal, an ammonium or substituted ammonium cation, wherein the compound decomposes under physiological conditions to release nitric oxide. Preferred compounds for this method are as herein described. In addition, compounds for this method include those where R is a phenyl or naphthyl group with an ortho or other substituent sufficiently bulky to force the NONO group out of coplanarity with the phenyl or naphthyl ring substituent.

Indications for NO compounds:

Primary Indications:

(a) uterine contractility disorders including dysmenorrhea, preterm labor and cervical incompetence (b) preeclampsia (c) hormone replacement therapy in women and men (i.e., estrogen and/or progesterone treatment for women, testosterone for men—used in elderly patients deficient in these hormones) NO donors could be used to replace estrogen and/or progesterone therapy in women and to replace testosterone in men. NO donors could also be used in combination with either estrogen and/or progesterone in women and in combination with testosterone in men.

(d) cardiovascular disease—including hypertension and atherosclerosis

Secondary (Potential) Indications:

(e) behavior (f) ovulation and implantation—contraception (g) induction of labor by softening the cervix (h) blood clotting by inhibiting coagulation (i) impotence (j) infections (k) topical applications to improve wound healing, skin texture and hair growth (l) lung function to dilate bronchioles (m) cancer In one aspect, this invention relates to a method of administering N-nitroso-N-substituted hydroxylamine salt derivatives as nitric oxide donors for the purposes of regulating a variety of biological functions, especially inducing smooth muscle relaxation. The amount of the nitric oxide donor being equivalent to that amount required to lower blood pressure about 10 to 50 mm Hg pressure. Usually, treatment is continued indefinitely or until otherwise prescribed.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE PREFERRED EMBODIMENTS

The present invention provides N-aryl-substituted N-nitrosohydroxylamine salts based on the compound 1 (C1) as having superior ability to act as nitric oxide donors.

$$R-N-O^- M^+ \qquad (1)$$
$$\phantom{R-}|$$
$$\phantom{R-}N=O$$

Table 2 includes a listing of these nitric oxide donors synthesized by the present inventors. They were characterized, inter alia, by infrared spectra, $^1$H-NMR and $^{13}$C-NMR spectra.

TABLE 2

Compounds synthesized having superior ability to act as donors of nitric oxide in vitro and in vivo N-Nitroso-N-(1-naphthyl)-hydroxylamine, ammonium salt (neocupferron)
Idem, sodium salt (via ionic exchange, from the preceding compound).
N-Nitroso-N-(2-methylphenyl)-hydroxylamine, salt
N-Nitroso-N-(2-methoxyphenyl)-hydroxylamine, salt
N-Nitroso-N-(2-ethylphenyl)-hydroxylamine, salt
N-Nitroso-N-(2-isopropylphenyl)-hydroxylamine, salt
N-Nitroso-N-(2,4-difluorophenyl)-hydroxylamine, salt
N-Nitroso-N-(2,5-difluorophenyl)-hydroxylamine, salt
N-Nitroso-N-(2-chlorophenyl)-hydroxylamine, salt
N-Nitroso-N-(2,3-dichlorophenyl)-hydroxylamine, salt
N-Nitroso-N-(2,4-dichlorophenyl)-hydroxylamine, salt
N-Nitroso-N-(2,5-dichlorophenyl)-hydroxylamine, salt
N-Nitroso-N-(2-bromophenyl)-hydroxylamine, salt
N-Nitroso-N-(5-fluoro-2-methylphenyl)-hydroxylamine, salt
N-Nitroso-N-(4-fluoro-2-methylphenyl)-hydroxylamine, salt
N-Nitroso-N-(4-choro-2-methylphenyl)-hydroxylamine, salt
N-Nitroso-N-(3-choro-2-methylphenyl)-hydroxylamine, salt Many earlier NO donors involve compounds in which the nitric oxide-releasing moiety is attached either to an oxygen or to a nitrogen atom. By contrast, the N-aryl-N-nitrosohydroxylamine salts of the present invention, as represented by (1) have this moiety attached to a carbon atom. The present inventors show that these compounds also exhibit NO releasing ability and significant biological effects. This NO releasing ability can be adjusted by varying the nature of the aryl group and its substituents.

A further advantage of the nitric oxide donor of the present invention is the fact that after release of NO, the by product is selected to be not carcinogenic. Structural variation permits fine tuning of the dose-response and releasing kinetics. Such variation also allows the attachment of the NO releasing moiety to biologically active groups which target specific organs or cells. Finally, the aryl group may interact with cell membranes, when adequately substituted, allowing control of penetration through biological barriers (e.g., blood brain barrier or placental barrier).

In order to obtain these new nitric oxide donors with higher stability and possibly no carcinogenic effect from secondary amines, the present inventors use: (i) cyclic secondary amines with steric shielding around the nitrogen atom, such as 2,2,6,6-tetramethylpiperidine or 2,2,5,5-tetramethylpyrrolidine; (ii) proline, hydroxyproline or their esters (either the natural L-isomer or the non-natural D-stereoisomer); in this case, the functionalized aminoacid carboxyl group may provide additional bioactive functions, as well as potential variability for introducing lipophilic esterified alcohol groups; (iii) diethanolamine or its intramolecular dehydration product (morpholine), which confers hydrophilic properties; (iv) bicyclic secondary amines such as 3-azabicyclo [3.2.2] nonane, whose NONO adducts would have the property that any disproportionations after splitting NO are forbidden by Bredt's rule (this rule states that double bonds involving bridgehead atoms are energetically unfavorable).

High levels of steroid hormones (mainly progesterone) during pregnancy appear to modulate either the production or action of nitric oxide. If nitric oxide is a transduction mechanism of steroid hormones, nitric oxide is expected to regulate other estrogen—and/or progesterone—dependent steps in reproduction and women's health, including ovulation, implantation, menstruation, climacterium, etc. In addition, some of the actions of the antihormones (e.g., antiprogestins) appear to be mediated through nitric oxide.

Based upon these considerations, nitric oxide donors are uterine relaxants and nitric oxide inhibitors will increase uterine contractility. In addition, nitric oxide inhibition substantially improves the action of antiprogesterone compounds to induce premature birth in rats and the same compounds alone induce premature birth in guinea pigs.

The existing data strongly indicate that the chronic steroid (estrogen and/or progesterone) effects on the blood vessels are mediated by nitric oxide. Inhibition of nitric oxide synthesis produces both atherosclerosis and osteoporosis in animal models (Moncada, et al., 1991). On the other hand, nitric oxide exhibits no direct effects on the endometrium in terms of proliferation and differentiation. Therefore, it will be possible for a suitable nitric oxide donor to replace steroids for hormone replacement therapy (HRT) in women. With this innovative strategy the major problems of HRT: endometrial hyperplasia and uterine bleeding can be avoided. The NO donors may be used, therefore, to prevent atherosclerosis and bone loss without inducing bleeding, (so called "no blood sector in HRT"). In addition, a suitable nitric oxide donor can by used for HRT, since these compounds do not exert hormone activities.

The pharmacologically active nitric oxide donors employed in this invention can be administered in admixture with conventional excipients, i.e., pharmaceutically acceptable liquid, semi-liquid or solid organic or inorganic carriers suitable, e.g., for parenteral or enteral application and which do not deleteriously react with the active compound in admixture therewith. Suitable pharmaceutically acceptable carriers include but are not limited to water, salt solutions, alcohols, vegetable oils, polyethylene glycol, gelatin, lactose, amylose, magnesium stearate, talc, silicic acid, viscous paraffin, perfume oil, fatty acid monoglycerides and diglycerides, pentaerythritol fatty acid esters, hydroxymethylcellulose, polyvinyl pyrrolidone, etc. The pharmaceutical preparations can be sterilized and, if desired, mixed with auxiliary agents, e.g., lubricants, preservatives, stabilizers, wetting agents, emulsifiers, slats for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, intrauterine devices and suppositories. Ampoules are convenient unit dosages. In a preferred aspect, the composition of this invention is adapted for ingestion.

For enteral application, particularly suitable are unit dosage forms, e.g., tablets, dragees or capsules having talc and/or a carbohydrate carrier or binder or the like, the carrier preferably being lactose and/or corn starch and/or potato starch; particulate solids, e.g., granules; and liquids and semi-liquids, e.g., syrups and elixirs or the like, wherein a sweetened vehicle is employed. Sustained release compositions can be formulated including those wherein the active compound is protected with differentially degradable coatings, e.g., by microencapsulation, multiple coating, etc.

Suitable for oral administration are, inter alia, tablets, dragees, capsules, pills, granules, suspensions, and solutions. The active compound is also suitable for transdermal patches and topical application. Each unit dose, i.e., each tablespoon of liquid or each tablet, or dragee contains, for example, 5–5000 mg of each active agent. Solutions for parenteral administration contain, for example, 0.01–1% of each active agent in an aqueous or alcoholic solution. The agents or combination can be administered as an admixture with any other optional active agent or as a separate unit dosage form, either simultaneously therewith or at different times during the day from each other.

The combination of active agents is preferably administered at least once daily (unless administered in a dosage form delivering the active agents continuously or sequentially). The typical dose is about 0.5 to 1000 mg of each active agent, although some less active agents may require much higher oral dosages, et., 500 to 10,000 mg, and others may require lower doses, e.g., 500–2,000 µg/kg/day. Doses for nitroglycerine typically are orally 2.5 mg 2× daily; sublingually, 0.8 mg 1–4× daily; and transdermally, 0.2–0.4 mg/hr. Since the $LD_{50}$ dosages of most of these active agents are known, a lower dosage regimen can be initiated and the dosage increased until a positive effect is achieved or a higher dosage regimen can initially be employed, e.g., in a crises situation, and the dosages regulated downward until the desired effect is achieved.

The following examples are included to demonstrate preferred embodiments of the invention. It should be appreciated by those of skill in the art that the techniques disclosed in these examples represent techniques discovered by the inventors to function well in the practice of the invention, and thus can be considered to constitute sundry modes of practice. However, those of skill in the art should, in light of the present disclosure, appreciate that many changes can be made in the specific disclosed embodiments to obtain a like or similar result without departing from the spirit and scope of the invention.

EXAMPLE 1

Synthesis of N-nitroso-N-aryl-substituted Hydroxylamine Derivatives

The synthetic approach for synthesizing the compounds of Table 2 consists in reducing an aromatic or heteroaromatic nitro or nitroso derivative to the corresponding hydroxylamine, either electrochemically, or with zinc powder and ammonium chloride in water or aqueous lower alcohols. The hydroxylamine is extracted with ethyl ether or another non-polar solvent and, after drying, is converted into the crystalline cupferron analog by treatment with gaseous ammonia and an alkyl nitrite. Finally, by means of an ion exchange column, an alkali metal or other desired cation may replace the ammonium cation.

This method, starting with nitro derivatives, was used for preparing a variety of compounds 1, where the R group is phenyl, or phenyl with the following substituents: 2-methyl; 2,3-dimethyl; 2-ethyl; 2-methoxy; 2-hydroxy; 2-fluoro; 2-chloro; 2,4-dichloro, 2,5-dichloro; 4-chloro-2-methyl; 2-acetyl; 2-bromo; α-naphthyl, 2-methyl-1-naphthyl, 2-hydroxy-1-naphthyl, or 1-hydroxy-2-naphthyl.

The preparation of neo-cupferron from α-nitronaphthylene, ammonia and hydrogen sulfide in ethanol, followed by treatment with butyl nitrite and ammonia in ethyl ether, according to O. Baudisch, was described by Smith (1938).

Alternative methods for obtaining compounds 1 or cupferron analogs (ammonium salts) are available: (1) the reaction of aryl Grignard reagents with nitric oxide followed by treatment with ammonia (Sand et al., 1903); (ii) the spin trapping of nitric oxide with a nitroso derivative, yielding an isolable N-aryl-N-nitrosonitroxide, which can then be reduced to 1 (Balaban et al., 1971, 1972, 1973, 1987); in a later publication, it was reported that nitrosobenzene and nitric oxide afforded cupferron in the presence of ammonia, and that the yield was increased when a reducing agent such as hydroquinol was added (Iida et al., 1978); (iii) the Sandmeyer reaction of aryldiazonium salts with nitric oxide in the presence of copper(II) and iron(II) salts, whereby an aryl radical reacts with NO leading to a nitroso derivative, followed by reaction with a second molecule of NO as in the preceding reaction (Minisci et al., 1964).

When the substituent is electron-donating (e.g methoxy, ethoxy, hydroxy, dimethylamino or diethylamino) the hydroxylamine and its salts are sensitive to air oxidation which converts them into deeply colored products (azo or azoxy derivatives), therefore they must be processed rapidly at lower temperatures, under inert atmosphere, and kept in the freezer. Such compounds with dialkylamino substituents may be considered as phenyl analogs of nitric oxide donors (Drago's NONOates) prepared from nitric oxide and secondary amines (Drago et al., 1961, 1962; Ragsdale et al., 1965; Longhi et al., 1962; Hansen et al. 1982). With other substituents, the dry crystalline products are stable at room temperature and can be kept at temperatures below 0° C.

Methods. The nitro derivative (0.1 mole) is stirred in an aqueous solution of ammonium chloride (0.1 mole). When the nitro derivative is solid with a melting point above 85° C. or has a very low water solubility, 50% percent aqueous ethanol may be used, and the initial temperature is raised to 60°–70°Zinc powder (0.2 mole) is added gradually under vigorous mechanical stirring so as to maintain the temperature around 70° C. due to the exothermicity of the reaction. After 60–90 minutes, the mixture is cooled below 35° C. and filtered with suction. The solid residue is thoroughly washed with 3–4 portions of diethyl ether; this ether is used for extracting the filtrate each time (Kamm and Marvel, 1941).

The combined ethereal extracts are dried over sodium sulfate, and cooled under 0° C. in an ice-salt mixture. A vigorous stream of gaseous ammonia is bubbled into the ethereal solution, and after 5–10 minutes, n-butyl nitrite is added in small portions during 15 minutes maintaining the cooling and the stream of $NH_3$. The cupferron analog (ammonium salt corresponding to 1) precipitates. If it separates as a liquid, one induces crystallization by scratching with a glass rod. The product is filtered off after being kept at 0° C. for 1–2 hrs, and washed thoroughly with diethyl ether (Marvel and Kamm, 1941).

A column packed with cationite which has been soaked in aqueous sodium hydrogen carbonate for 24 hrs and then rinsed with distilled water is used for exchanging ammonium with sodium cations: a concentrated solution of the cupferron analog in water or 50% aqueous ethanol is passed through the column; elution is performed with the same solvent, monitoring the UV absorption at 280 nm. The eluates are combined and the solvent is removed by using a rotary evaporator under vacuum at 30°–40° C. or freeze drying techniques for heat-sensitive compounds. Overall yields vary between 20 and 85%.

The most preferred NO donors related to cupferron have either ortho-substituents (e.g., 2-chloro and 2-methoxy), or have types of bulky groups forcing the NONO group out of coplanarity with the aromatic ring: examples thereof include neocupferron analogs (N-nitroso-α-naphthylhydroxylamine salts), and substituted heterocyclic analogs.

During the preparation of such sterically hindered analogs of cupferron it was observed that the precipitation of ammonia salts on introducing gaseous ammonia and alkyl nitrite into the ethereal solution of the N-arylhydroxylamine occurs more slowly than in the absence of bulky ortho-substituents; therefore one has to filter off the products only after keeping the solution at 0° for 4–12 hours.

EXAMPLE 2

Biological Effects of N-nitroso-N-substituted Hydroxylamines

Figure 1:
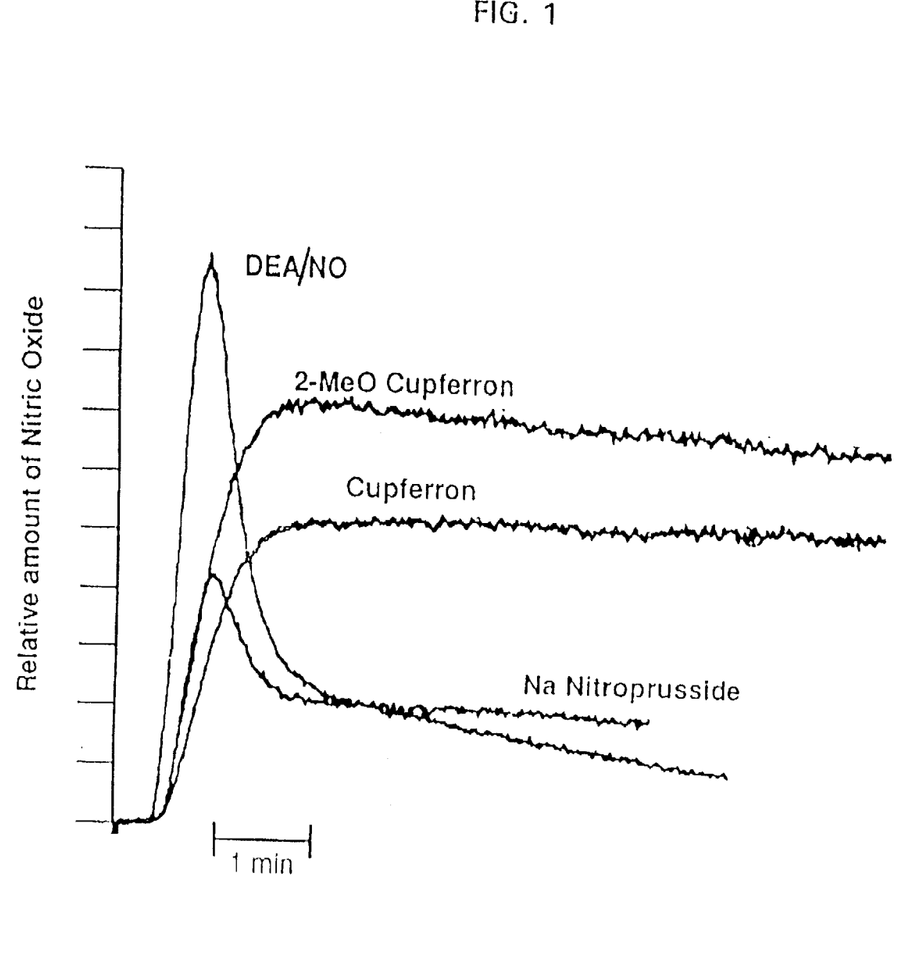
FIG. 1 shows tracings of the relative amount of NO released from various NO donors versus time, as determined by chemoluminescence. DEA/NO is diethylenetriamine/NO at a concentration of $10^{-4}$M. 2-Methoxycupferron, cupferron, and sodium nitroprusside were present in a concentration of $10^{-2}$M.
Figure 2:
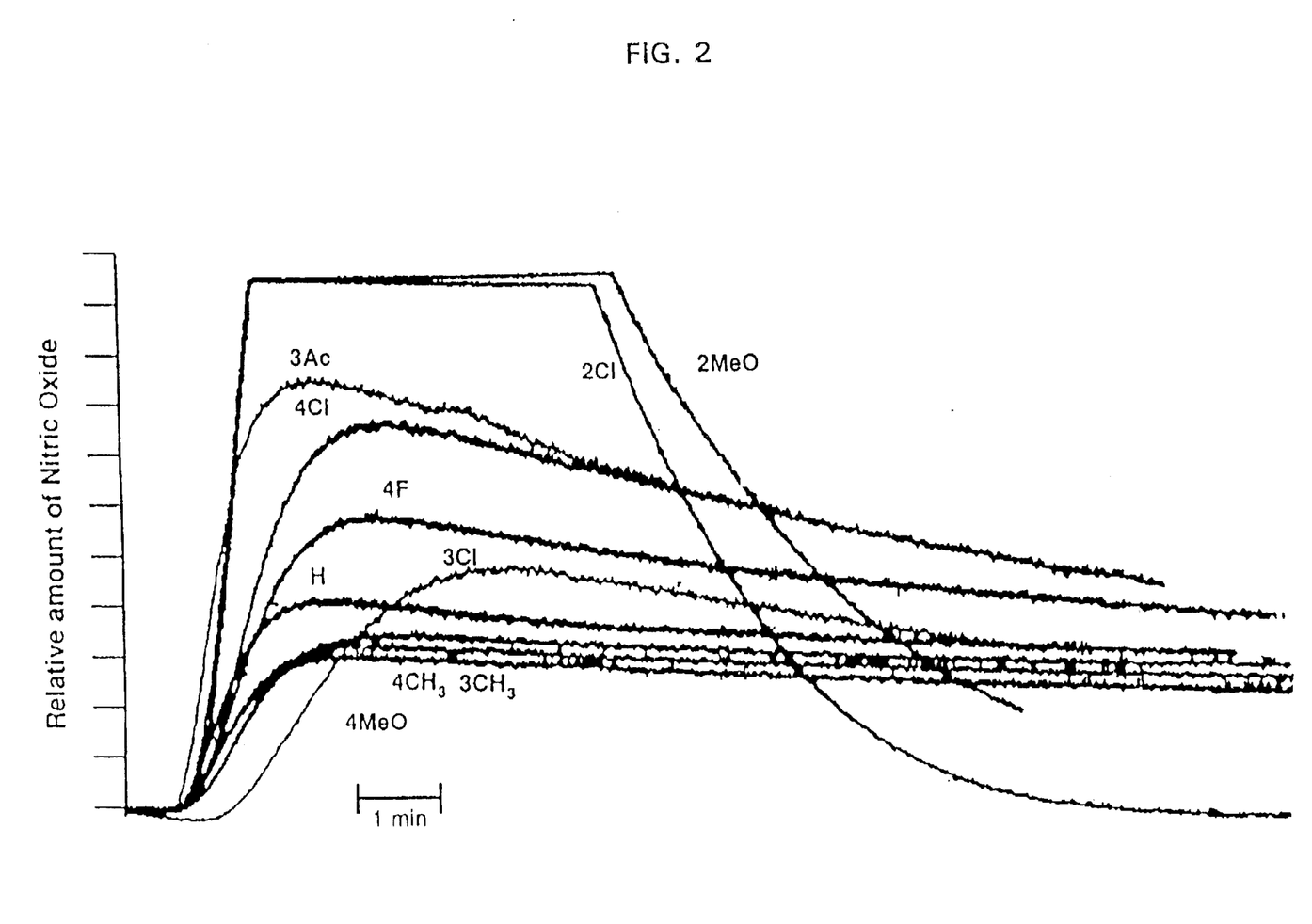
FIG. 2 shows relative amounts of NO released from various N-nitrosohydroxylamine compounds. The label for each data line indicates the chemical group and the position of the phenyl ring where the group is attached.

FIGS. 1 and 2 show release of nitric oxide from various derivatives of N-nitroso-N-substituted hydroxylamine as tested in vitro in comparison to DEA-NO and Na nitroprusside, two other nitric oxide donor compounds. These results show that some of the compounds slowly release NO while others quickly release it.

Figure 3A:
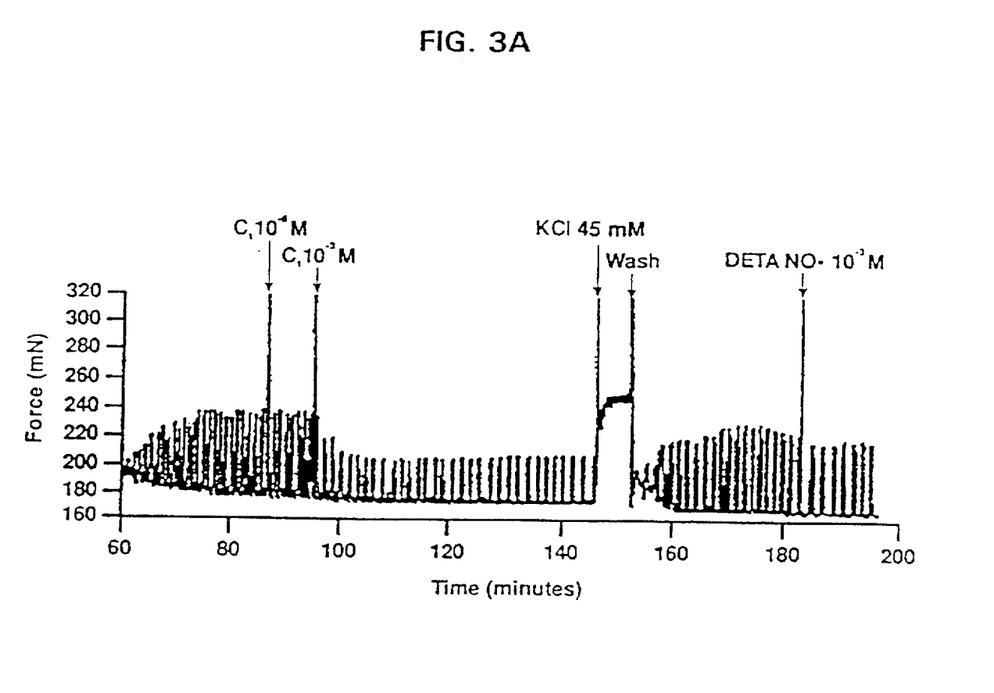
FIG. 3A and FIG. 3B show contractile recordings for separate rat uterine strips in vitro. Each upward deflection represents a contraction. Arrows indicate addition of agents. $C_1$ is cupferron. DETA/NO is diethylenetriamine/NO.
Figure 3B:
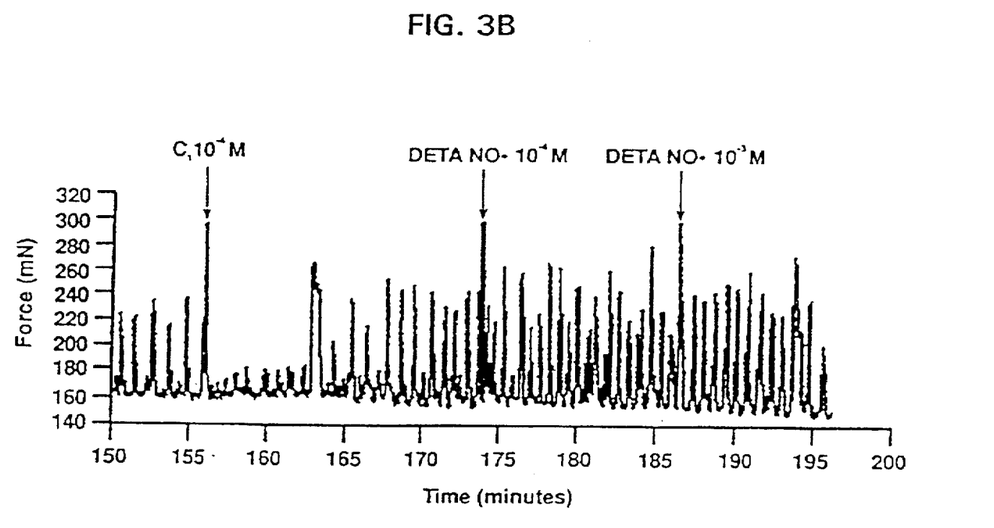
Figure 4A:
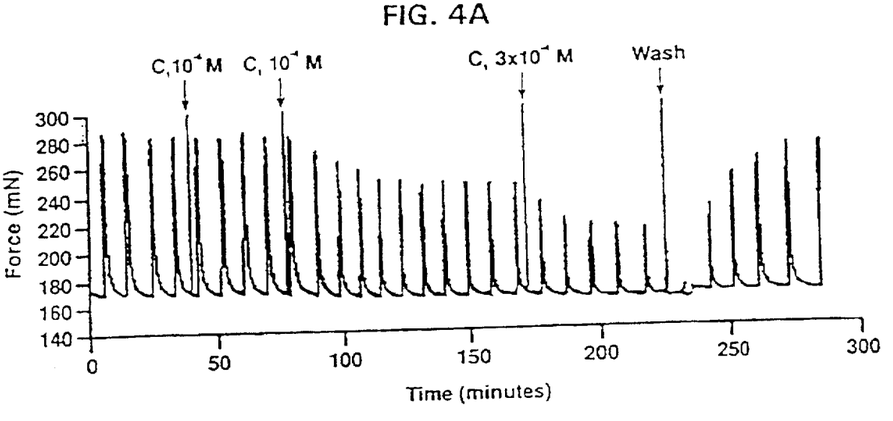
FIG. 4A, FIG. 4B and FIG. 4C depict contractile recordings that show the effects of cupferron (C1) on contractions of human uterine strips in vitro.
Figure 4B:
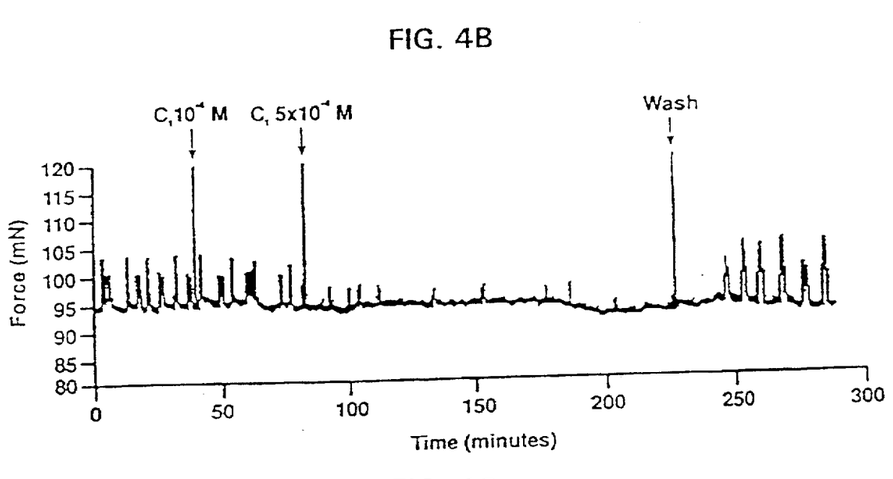
Figure 4C:
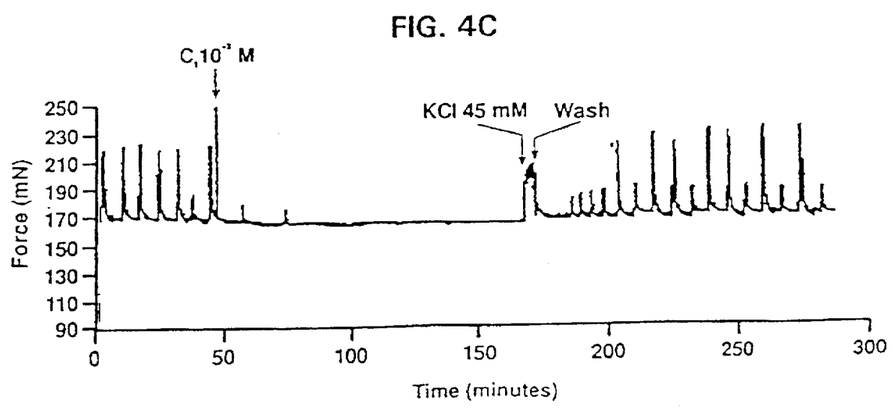
Figure 5A:
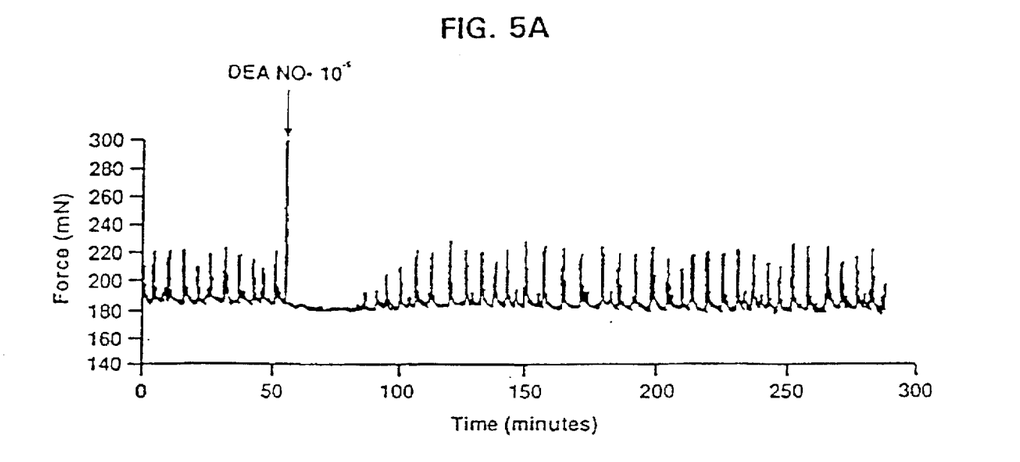
FIG. 5A, FIG. 5B, and FIG. 5C depict contractile recordings that show the effects of DETA/NO, a nitric oxide donor, on contracting human uterine strips in vitro.
Figure 5B:
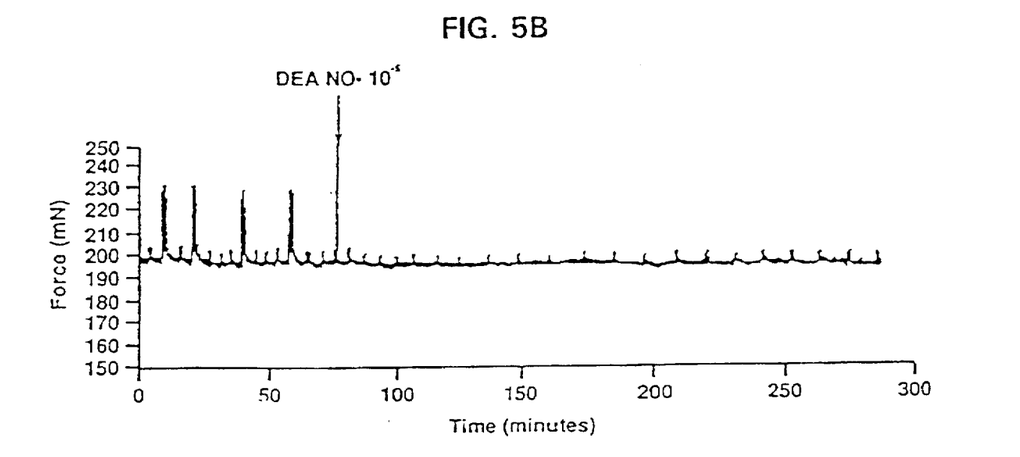
Figure 5C:
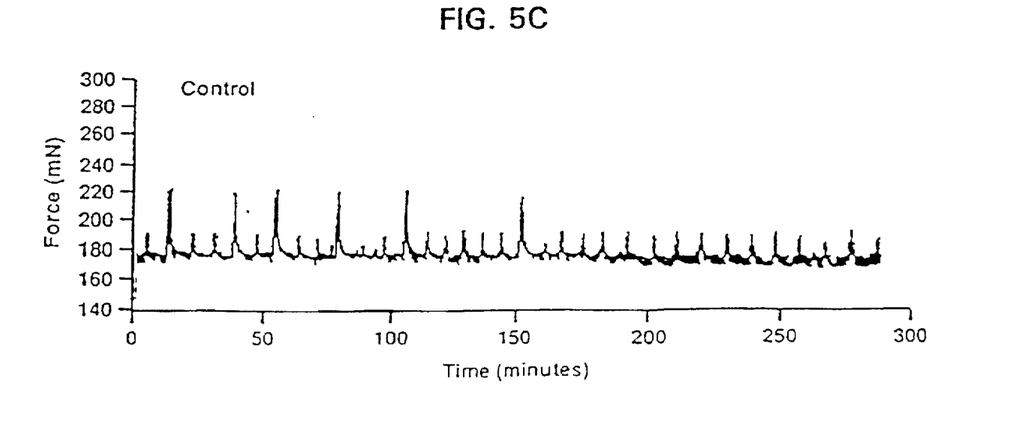

Several N-nitroso-N-arylhydroxylamine derivatives were tested on contractions of uterine strips from rats and humans in vitro. The derivative produced substantial relaxation responses in a dose-dependent manner consistent with the evidence that the compound is a nitric oxide donor (FIGS. 3, 4 and 5). The response was quickly reversible following washing.

The effects of the derivatives were also compared to DETA/NO, a known nitric oxide donor compound. The N-nitroso-N-arylhydroxylamine compounds were more potent than DETA/NO on the rat uterus but it was less potent on the human uterus (FIGS. 3, 4 and 5). However, the duration of action of the derivative was long with washing required to terminate an inhibitory action. In these experiments uterine strips (about 1 mm×0.5 mm×15 mm) (FIGS. 3 to 5) from rats (FIG. 3) or humans (FIG. 4) were dissected from the whole uterine and the contraction studies i muscle baths. Each upward deflection in the figures (FIGS. 3 to 5) represents a contraction and downward movements are equal to relaxation phases. Addition of agents to the muscle baths are indicated by vertical lines.

Figure 6:
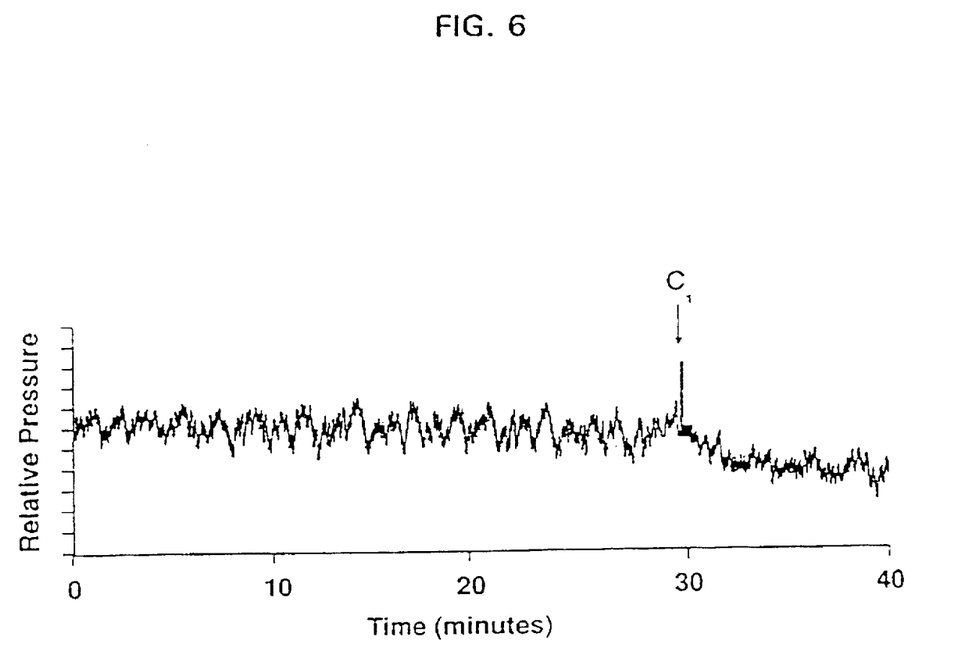
FIG. 6 shows intrauterine pressure recorded from a pregnant rat at day 19 of gestation. Addition of cupferron (C1) resulted in a substantial decrease in pressure indicating uterine relaxation.

The compound was tested on intact animals to determine if the derivative inhibited uterine contractions. A catheter was placed in the uterine cavity to measure pressure. FIG. 6 shows the inhibitory responses on pressure signals from the uterus recorded from pregnant rats at day 20 gestation. Rats were injected with the cupferron derivative (1 to 5 mg IP) and it produced a dramatic fall in intrauterine pressure suggesting an inhibition of uterine contractility. Similarly, all rats demonstrated signs of vasodilation and bronchodilation.

A human female suffering from conditions of a nitric oxide deficiency, such as hypertension, preeclampsia, or uterine hypercontractility could be treated with N-nitroso-N-arylkydroxylamine compounds described herein to relieve such disorders.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Ahokas et al., *Am. J. Obstet. Gynecol.*, 164:242, 1991.
Balaban et al., *J. Magnetic Resonance*, 9:1–7, 1973.
Balaban, *Rev. Roum. Chim.*, 16:725–737, 1971.
Balaban and Istratoiu, *Tetrahedron Lett.*, 1879–1881, 1973.
Balaban et al., *Rev. Roum. de Chimie*, 16:721–723, 1971.
Balaban et al., *Tetrahedron*, 43:405–408, 1987.
Balaban et al., *Rev. Roum, Chim.*, 16:721–723, 1971.
Balaban et al., *J. Magn. Reson.*, 9:1–7, 1973.
Balaban and Negoita, *Rev. Roum. Chimie*, 17:1227–1234, 1972.
Balaban and Negoita, *Rev. Roum. Chimie*, 16:721–723, 1971.
Balaban et al., *Tetrahedron*, 43:405–408, 1987.
Bredt and Synder, *Proc. Natl. Acad. Sci. USA*, 87:682–685, 1990.
Drago et al., *J. Am. Chem. Soc.*, 83:4337, 1961.
Drago and Karstetter, J. Am. Chem. Soc., 83:1819, 1961.
Drago, "Reactions of nitrogen(II) oxide, in Free Radicals in Inorganic Chemistry," Advances in Chem Series No. 36, Amer. Chem. Soc., Washington, D.C., 1962, pp. 143, *Amer. Chem. Soc.*, 143, 1962.
Furchgott and Zawadzki, *Nature*, 288:373–376, 1980.
Garfield and Yallampalli, "Control of myometrial contractility and labor." In: Basic Mechanisms Controlling Term and Preterm Birth. eds.: K Chwalisz, RE Garfield, Springer-Verlag, New York, 1993.
Hansen et al., In: "N-Nitroso Compounds: Occurrence and Biological Effects" (Eds. Bartsch H., O'Neill IK, Castegnaro M and Okada M) IARC Publication No. 41, International Agency for Research on Cancer, Lyon, p. 21.
Ignarro, *Biochem. Pharmacol.*, 41:485–490, 1991.
Iida et al., *Chem. Abstr.*, 89:179627, 1978.
Izumi et al., *Am. J. Obstet. Gynecol.*, 169:1327–1337, 1993.
Kamm and Marvel, *Org. Synth. Coll.*, 1:177, 1941.
Kasten et al., *Proc. Natl. Acad. Sci. USA*, 91:3569–3573, 1994.
Keefer et al., Chemistry of the "NONOates", unusual N-nitroso compounds formed by reacting nitric oxide with nucleophiles, in "Nitrosamines and Related N-Nitroso Compounds: Chemistry and Biochemistry" (Eds. RN Loeppky and CJ Michedja). ACS Symp. Series No. 553, Amer. Chem. Soc., Washington, D.C., 136–146, 1994.
Keefer et al., *Chem. Abstr.*, 113:145344, 1990.
Lees et al., *Lancet*, 343:1325–1326, 1994.
Longhi et al., *Inorg. Chem.*, 1:768, 1962.
Marvel and Kamm, *Org. Synth. Coll.*, 1:445, 1941.
Minisci and Galli, *Chimica e Industria (Milano)*, 46:423, 1964.
Moncada et al., *Pharmacol. Rev.*, 43:109–142, 1991.
Negoita et al., *Tetrahedron Lett.*, 1877–1878, 1973.
Pilipenko et al., *Kupferon* (175 pp. book in Russian), Nauka, Moscow, 1988.
Pinto et al., *Am. J. Obstet. Gynecol.*, 164:507–513, 1991.
Ragsdale et al., *Inorg. Chem.*, 14:420, 1965.
Roberts et al., *Am. J. Obstet. Gynecol.*, 161(5):1200, 1989.
Saavedra et al., *J. Org. Chem.*, 57:6134, 1992.
Sand and Singer, *Liebigs Ann. Chem.*, 329:190, 1903.
Smith, Cupferron and Neo-cupferron, G. F. Smith Chem. Co., Columbus, Ohio, 1938.
U.S. Pat. No. 4,954,526, Sep. 4, 1990.
U.S. Pat. No. 5,039,705, Aug. 13, 1991.
U.S. Pat. No. 4,535,154, Aug. 13, 1985.
U.S. Pat. No. 5,250,550, Oct. 5, 1993.
U.S. Pat. No. 5,212,204, May 18, 1993.
U.S. Pat. No. 5,185,376, Feb. 9, 1993.
U.S. Pat. No. 5,155,137, Oct. 13, 1992.
U.S. Pat. No. 5,208,233, May 4, 1993.
Yallampalli et al., *Endocrinol.*, 133(4):1899–1902, 1993.
Yallampalli and Garfield, *Am. J. Obstet Gynecol.*, 169:1316–1320, 1993.
Yallampalli et al., *Am. J. Obstet Gynecol.*, 170:175–185, 1993.

What is claimed is:

1. A method of inhibiting uterine contractions in a subject comprising administering a therapeutically effective amount to the subject of of a nitric oxide donor having the structure $$\begin{array}{c} R-N-O^- M^+ \\ | \\ N=O \end{array}$$

where R is 2-methoxyphenyl and M is an alkali metal, an alkaline-earth metal, an ammonium or substituted ammonium cation.

2. A method of supplying nitric oxide to a subject comprising administering to the subject a pharmacologically effective amount of a compound having the structure $$\begin{array}{c} R-N-O^- M^+ \\ | \\ N=O \end{array}$$

where
R is 2-methoxyphenyl; and
M is an alkali metal, an alkaline-earth metal, an ammonium or substituted ammonium cation,
wherein the compound decomposes under physiological conditions to release nitric oxide.

* * * * *